United States Patent
Senn

(10) Patent No.: US 8,568,976 B2
(45) Date of Patent: *Oct. 29, 2013

(54) PROINFLAMMATORY NUCLEIC ACIDS

(75) Inventor: Joseph Senn, Charleston, SC (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/323,461

(22) Filed: Dec. 12, 2011

(65) Prior Publication Data

US 2012/0295272 A1   Nov. 22, 2012

Related U.S. Application Data

(63) Continuation of application No. 11/404,544, filed on Apr. 13, 2006, now Pat. No. 8,101,345, which is a continuation-in-part of application No. 11/090,828, filed on Mar. 25, 2005, now abandoned.

(51) Int. Cl.
  *C12Q 1/68*   (2006.01)

(52) U.S. Cl.
  USPC .......................................................... 435/6.1

(58) Field of Classification Search
  USPC .......................................................... 435/6.1
  See application file for complete search history.

(56) References Cited

U.S. PATENT DOCUMENTS

| | | | |
|---|---|---|---|
| 8,101,345 B1 * | 1/2012 | Senn .............................. | 435/6.1 |
| 2003/0165875 A1 | 9/2003 | Colonna et al. | |
| 2004/0180847 A1 | 9/2004 | Dobie et al. | |

OTHER PUBLICATIONS

Becker, "CpG ODNs Treatments of HIV-1 Infected Patients May Cause the Decline of Transmission in High Risk Populations—A Review, Hypothesis and Implications" Virus Genes (2005) 30(2):251-266.

Dalpke et al., "CpG DNA in the Prevention and Treatment of Infections" Biodrugs (2002) 16(6):419-431.
Dandimalla et al., "Toll-like receptor 9: modulation of recognition and cytokine induction by novel synthetic CpG DNAs" Biochem. Soc. Trans. (2003) 31(3):654-658.
Daws et al., "Pattern recognition by TREM-2: Binding of Anionic Ligands" The Journal of Immunology (2003) 171:594-599.
Harandi et al., "CpG DNA as a potent inducer of mucosal immunity: Implications for immunoprophylaxis and immunotherapy of mucosal infections" Current Opinion in Investigational Drugs (2004) 5(2):141-145.
Hatao et al., "Prolonged Toll-like receptor stimulation leads to down-regulation of IRAK-4 protein" J. Leukoc. Biol. (2004) 76:904-908.
Henry et al., "Chemically Modified Oligonucleotides Exhibit Decreased Immune Stimulation in Mice" Journal of Pharmacology and Experimental Therapeutics (2000) 292:468-479.
Gangloff et al., "Toll-Like Receptors and Immune Response in Allergic Disease" Clinical Reviews in Allergy and Immunology (2004) 26:115-125.
Jiang et al., "Enhancing immunogenicity by CpG DNA" Curr. Opin. Mol. (2003) 5(2):180-185.
Rothenfusser et al., "Recent advances in irnmunostimulatory CpG oligonucleotides" Curr. Opin. Mol. Ther. (2003) 5(2):98-106.
Senn et al., "Non-CpG-Containing Antisense 2'-Methoxyethyl Oligonucleotides Activate a Proinflammatory Response Independent of Toll-Like Receptor 9 or Myeloid Differentiation Factor 88" The Journal of Pharmacology and Experimental Therapeutics (2005) 314:972-979.
Vollmer et al., "Oligodeoxynucleotides lacking CpG dinucleotides mediate Toll-like receptor 9 dependent T helper type 2 biased immune stimulation" Immunology (2004) 113:212-223.
Wang et al., "Synthetic Oligodeoxynucleotides Containing Deoxycytidyl-Deoxyguanosine Dinucleotides (CpG ODNs) and Modified Analogs as Novel Anticancer Therapeutics" Curr. Pharma. Des. (2005) 11:2889-2907.

* cited by examiner

*Primary Examiner* — Brian Whiteman
(74) *Attorney, Agent, or Firm* — Knobbe, Martens, Olson & Bear, LLP

(57) ABSTRACT

The present invention provides compositions and methods for identifying and utilizing proinflammatory nucleic acids. In particular, this invention relates to compounds, particularly oligonucleotides, which exert their effect through triggering receptors expressed by myeloid cells (TREMs), specifically TREM 2.

21 Claims, No Drawings

PROINFLAMMATORY NUCLEIC ACIDS

CROSS REFERENCE TO RELATED APPLICATIONS

This application is a continuation of U.S. application Ser. No. 11/404,544 filed Apr. 13, 2006, now U.S. Pat. No. 8,101,345, which is a continuation-in-part of U.S. patent application Ser. No. 11/090,828 filed on Mar. 25, 2005, now abandoned, each of which is incorporated herein by reference in its entirety.

SEQUENCE LISTING

A paper copy of the sequence listing and a computer-readable form of the sequence listing, on diskette, containing the file named CORE0038USC1SEQ.txt, created on Dec. 8, 2011, which is 4 KB in size. The information in the electronic format of the sequence listing is incorporated herein by reference in its entirety.

BACKGROUND OF THE INVENTION

Oligonucleotides with a bacterial-like "CpG" have been shown to trigger proinflammatory responses through activation of Toll-like receptor 9 (TLR9). This results in activation of a signal transduction pathway involving the Myd88 adaptor protein, and downstream activation of mitogen activated protein kinase (MAPK) family members and the nuclear factor (NF)-kappa B pathway. This stimulation leads to an increased production of cytokines including interferons, interleukin (IL)-6 and 12, tumor necrosis factor-alpha (TNF-α), chemokines, costimulatory molecules, and antigen presentation on antigen presenting cells (APCs). This process further stimulates adaptive immunity and potentiates a T-helper 1 (Th1) type response.

The cellular and humoral immune responses stimulated by exposure to CpG oligonucleotides is likely a result of the relative abundance of unmethylated CpG motifs in bacteria and other pathogens, as compared to mammalian DNA, in which such motifs are rare. The human immune system has apparently evolved to recognize CpG sequences as early signs of infection and to initiate an immediate immune response against pathogens without causing adverse reactions frequently seen with other proinflammatory agents. Thus, CpG containing nucleic acids, relying on this innate immunity, can utilze a distinct and natural pathway for immune therapy.

Oligonucleotides containing CpG motifs have been developed to exploit this process for use for the prevention and treatment of infections (Dalpke et al., BioDrugs. 2002; 16:419-31, incorporated herein by reference); vaccine adjuvants (Rothenfusser et al., Curr Opin Mol. Ther. 2003. 5:98-106, incorporated herein by reference), including those for the induction of mucosal immunity (Curr Opin Investig Drugs. 2004.5:141-5); allergy (Gangloff and Guenounou. Clin Rev Allergy Immunol. 2004. 26:115-25, incorporated herein by reference); cancer (Jaing et al., Curr Opin Mol. Ther. 2003. 5:180-5; Wang et al., Curr Pharm Des. 2005. 11:2889-907, both incorporated herein by reference); HIV (Becker. Virus Genes. 2005. 30:251-66, incorporated herein by reference); and autoimmune diseases such as lupus (Lenert, Clin Exp Immunol. 2005. 140:1-10, incorporated herein by reference). Importantly proinflammatory CpG motifs show optimal activity in both mouse and human systems without the need to change sequences, suggesting an overriding of the species-dependent specificity of the receptor by the use of synthetic motifs (Kandimalla et al., Biochem Soc Trans. 2003. 31:654-8, incorporated herein by reference).

The activity of CpG proinflammatory nucleic acids can be tested in various immune cell assays. Such methods are described in detail in PCT Published Patent Applications PCT/US95/01570 (WO 96/02555) and PCT/US97/19791 (WO 98/18810) claiming priority to U.S. Ser. Nos. 08/386,063 and 08/960,774, filed on Feb. 7, 1995 and Oct. 30, 1997 respectively. The methods require the use of primary cells from either mice or humans. The effectiveness of the assay on determining the activity of a nucleic acid is dependent upon the appropriate receptors and signaling pathways being present in the cells used.

Recently, research has shown that oligonucleotides devoid of CpG motifs are capable of eliciting a proinflammatory response in vivo and in vitro. Using a mouse knockout model, it was demonstrated that the response to these oligonucleotides is mediated by TLR9. It was suggested that the immunostimulatory motif consists of a 5'-TC dinucleotide in a thymidine rich background, preferably about at least 35% (Vollmer et al., Immunol. 2004. 113:212-223, incorporated herein by reference). The motif was found to stimulate B-cell activation, but lacked a Th1-like cytokines and chemokines.

Oligonucleotides intended for antisense applications are designed to avoid CpG and other proinflammatory motifs that induce a proinflammatory response by using various chemical modifications (i.e. 2'MOE sugars and methylation of cytosine residues) (Henry et al., J. Pharmacol. Expt. Thera. 2000. 292: 468-479). However, some oligonucleotides have immunostimulatory activity, despite having no identifiable proinflammatory motifs and/or containing modified nucleobases to reduce immunostimulatory activity. Such activity is often not identified until the oligonucleotide is administered to an animal. An in vitro method for identifying such oligonucleotides would be desirable.

SUMMARY OF THE INVENTION

The invention includes the finding that non-CpG and non-5'-TC oligonucleotides are effective in mediating immune stimulatory effects. Moreover, these effects are independent of TLR9. Thus the invention includes proinflammatory oligonucleotides that act via a TLR9 independent pathway, and their use for stimulating the immune system. The invention is particularly useful for applications similar to those in which CpG oligonucleotides are used.

The invention includes the discovery that TREM-2 is specifically stimulated by nucleic acids including those containing 2'-methoxyethoxy (2'-O—$CH_2CH_2OCH_3$, also known as 2'-O-(2-methoxyethyl) or 2'-MOE) modifications. Non-CpG compounds retained the ability to activate a proinflammatory response in the knockout animals lacking a functional TLR9 signaling pathway, demonstrating a TLR9-independent mechanism of action by non-CpG proinflammatory oligonucleotides. The invention includes the discovery that non-CpG oligonucleotides exert their effect through Triggering Receptor Expressed by Myeloid cells 2 (TREM2). TREM2 activates monocyte-derived dendritic cells and regulates osteoclast development. TREM2 deficiency leads to severe disease that is characterized by bone cysts and demyelination of the central nervous system. The presence of TREM-2 on distinct cell lines from TLR9 means that the oligonucleotides can effect different cell populations.

The invention includes a method for screening for proinflammatory oligonucleotides that activate the TREM2 pathway. The discovery of the role of TREM-2 allows for the development of the method of the instant invention as proinflammatory oligonucleotides were not known to act via TREM-2. The method includes a cell line expressing a TREM-2 extracellular domain functionally linked to an intracellular signaling domain. The TREM-2 intracellular domain can be the native (e.g., wild type) intracellular domain; alternatively, the TREM-2 domain can be linked to a heterologous intracellular signaling domain (e.g., CD3ζ). The intracellular domain is capable of activating a downstream target or reporter construct upon binding of a proinflammatory nucleic acid to the extracellular TREM2 domain. Activation of the downstream target or expression from the reporter construct is indicative of binding of the oligonucleotide to the TREM2 extracellular binding domain. The cell line and method were shown to predict proinflammatory activity of oligonucleotides comparable to bone marrow cells, which in turn, were comparable to data derived from whole animal models (i.e., mice). This allows for analysis of proinflammatory activity in vitro.

The invention includes nucleic acids that possess proinflammatory activity, especially non-CpG containing oligonucleotides, independent of TLR9 signaling. Thus, it is possible to induce an immune response using the disclosed nucleic acids. These findings have important implications for the clinical development of proinflammatory nucleic acids.

DETAILED DESCRIPTION AND PREFERRED EMBODIMENTS

CpG motifs, 5'-TC motifs, and highly repetitive sequences are well known and easily identifiable by their sequences. Oligonucleotides having CpG motifs are useful for their stimulation of a proinflammatory response via the TLR9 pathway, making them useful for the prevention, amelioration, and/or treatment of disease. CpG motifs are also useful as vaccine adjuvants. However, oligonucleotides including such motifs are limited in their usefulness as antisense oligonucleotides designed to act through a sequence specific, hybridization mechanism or other target specific pathway.

In the design of antisense oligonucleotides, known proinflammatory motifs are avoided. However, upon administration into animals, some oligonucleotides have been found to have proinflammatory activity despite lacking any known proinflammatory motifs. By the identification of the pathway through which these oligonucleotides have their proinflammatory effects, it is possible to develop a screening method to identify such oligonucleotides in vitro.

RAW 264.7 cells are a mouse macrophage cell line established from a tumor induced in a male mouse by intraperitoneal injection of Abelson Leukemia Virus (A-MuLV) (Raschkea et al., Cell. 15:261-267. 1978) were used. The cells are capable of antibody dependent lysis of sheep erythrocytes and tumor targets. They also express some TLRs, including TLR9 (Hatao et al., J. Leukoc. Biol. 76:904-908. 2004). Cells were transiently transfected with an expression vector coding for a TREM2 extracellular domain functionally linked to a Nuclear Factor of Activated T-cells (NFAT) intracellular activation domain. Proinflammatory activity was determined by NFAT activation as determined by ELISA assay. The cell line was found to have both positive and negative predictive value for proinflammatory activity as previously determined in mice and in primary mouse bone marrow cells. The method provides an in vitro system that does not require primary cells to test for TLR9 independent proinflammatory activity of oligonucleotides. This allows for the screening of oligonucleotides intended for uses wherein proinflammatory activity is not desired, without the cost and effort required for animal testing or the preparation of primary cells.

The invention includes a method for the identification of proinflammatory oligonucleotides comprising generation of a cell line functionally expressing a TREM-2 extracellular domain and an intracellular signaling domain. The TREM-2 extracellular domain can be linked to a TREM-2 intracellular domain (e.g., wild type protein); alternatively, the TREM-2 extracellular domain can be linked to a heterologous intracellular signaling domain (e.g., CD3ζ). The cell line also contains a reporter construct comprising a cis-acting DNA consensus element (e.g., transcription factor binding site or enhancer) sensitive to activation of the intracellular domain, wherein the cis-acting DNA consensus element is functionally linked to a reporter gene coding sequence. Upon binding of a proinflammatory oligonucleotide to the TREM-2 binding domain, the intracellular signaling domain is activated. This activation can result in the direct activation of a transcription factor (e.g., NFAT) or enhancer that binds the cis-acting DNA consensus sequence directly. Alternatively activation can result in the initiation of a signaling cascade to cause the activation of a transcription factor that binds the cis-acting DNA consensus sequence. The expression construct for the TREM-2 chimera and the reporter constructs may be transiently and/or stably transfected into the cells. Methods of both transient and stable transfection are well known to those skilled in the art, and are dependent on factors such as cell type. The cells containing the expression and reporter constructs are contacted with the oligonucleotides to be assayed for proinflammatory activity, preferably for about 2 to about 24 hours at a concentration of about 0.01 ug/ml to about 100 ug/ml, more preferably from about 1 ug/ml to 100 ug/ml. Depending on the reporter gene used, media from the cells is collected (e.g., secreted alkaline phosphatase (SEAP)) or cells are harvested and lysed (e.g., beta-galactosidase, luciferase). Presence of the reporter gene is detected using commercially available kits and/or by methods well known to those skilled in the art. The reporter gene used and its method of detection are not a limitation of the invention.

Reporter systems and detection kits for use in the instant invention are well known to those skilled in the art. A number of cell lines stably expressing reporter constructs are available commercially from a number of sources (e.g., Invitrogen™, Cambridge Bioscience, and Panomics). Cis-acting DNA consensus sequences used in the commercially available lines include AP-1, CREB, NFAT, NF-kappa B, SRF, STAT1, STAT3, and TAD functionally linked to reporter genes including luciferase and beta-galactosidase. Such cell lines allow for the formation of a TREM-2 chimera with any corresponding intracellular activation domain for use in the method of the instant invention. Methods of assaying for the expression from the reporter gene can be performed using methods provided by the manufacturer.

The invention includes the use of the non-CpG containing oligonucleotides in a manner similar to CpG oligonucleotides for the stimulation of a proinflammatory response for the prevention, amelioration, and/or treatment of disease, or as a vaccine adjuvant. Due to the different relative levels of activity of CpG and non-CpG oligonucleotides in the stimulation of a proinflammatory response, and the different mechanism of action of the two classes of proinflammatory oligonucleotides, one may be preferred over the other in specific conditions. Moreover, the proinflammatory activity of the non-CpG containing oligonucleotides is independent of TLR9 and Myd88, both of which are involved in the immune response to CpG-containing oligonucleotides; therefore, it may be useful to promote a distinct immune response from that prompted by CpG oligonucleotides.

The invention includes a pharmaceutical composition comprising an effective amount for stimulating an immune response of isolated non-CpG nucleic acids, and a pharmaceutically acceptable carrier. Another aspect provided herein is a composition of matter, comprising a non-CpG proinflammatory nucleic acid. In other embodiments, the proinflammatory nucleic acid may contain 2'-methoxyethoxy modifications.

The proinflammatory nucleic acids in some embodiments have a nucleotide backbone that includes at least one backbone modification, such as a phosphorothioate modification. The nucleotide backbone may be chimeric, or the nucleotide backbone is entirely modified.

In another aspect the invention is a composition of a proinflammatory nucleic acid and an antigen.

Another composition is an proinflammatory nucleic acid and an anti-microbial agent. The anti-microbial agent can be selected from the group consisting of an anti-viral agent, an anti-parasitic agent, an anti-bacterial agent and an anti-fungal agent.

It should be understood that when it is useful to administer one or more non-CpG oligonucleotides and one or more CpG oligonucleotides, it may also be desirable to co-administer one or more non-CpG oligonucleotides together with one or more physically separate CpG or non-CpG oligonucleotides or provide all motifs on the same oligonucleotide. By co-administration it is intended that the nucleic acids be administered close enough in time to one another to achieve a combined benefit of both oligonucleotides, preferably more than the benefit achieved by administering each of the oligonucleotides alone at the same dose.

CpG oligonucleotides have, in general, the formula $5'X_1X_2CGX_3X_43'$, wherein $X_1$, $X_2$, $X_3$ and $X_4$ are nucleotides and wherein at least the C of CpG is unmethylated. Suitable CpG oligonucleotides are 8-100 nucleotides in length and have modified backbones. Particular structures are detailed in the references cited herein, the disclosures of which are incorporated herein in their entirety.

Provided herein are pharmaceutical compositions and kits which contain at least one non-CpG proinflammatory oligonucleotide, or at least one CpG oligonucleotide and at least one non-CpG oligonucleotide, physically separate from the CpG oligonucleotide. The pharmaceutical preparations are in effective amounts and typically include pharmaceutically acceptable carriers, all as set forth in detail herein. The kits include at least one container containing at least one non-CpG oligonucleotide. The same container, or in other embodiments, a second container, may contain an oligonucleotide with a CpG motif. The kit also contains instructions for administering the oligonucleotides to a subject. The kits also may include a container containing a solvent or a diluent.

The composition may optionally include a pharmaceutical carrier and/or be formulated in a delivery device.

A vaccine formulation is provided. The vaccine includes any of the compositions of the invention in combination with an antigen.

Another aspect is a method of stimulating an immune response. The method involves administering an proinflammatory nucleic acid to a subject in an amount effective to induce an immune response. The proinflammatory nucleic acid is administered orally, locally, in a sustained release device, mucosally to a mucosal surface, systemically, parenterally, or intramuscularly. When the proinflammatory nucleic acid is administered to the mucosal surface it may be delivered in an amount effective for inducing a mucosal immune response or a systemic immune response. In suitable embodiments the mucosal surface is selected from the group consisting of an oral, nasal, rectal, vaginal, and ocular surface.

In some embodiments the method includes exposing the subject to an antigen wherein the immune response is an antigen-specific immune response. The antigen may be encoded by a nucleic acid vector which can be delivered to the subject.

In still another embodiment, the disclosed nucleic acids are useful for treating cancer. The proinflammatory nucleic acids are also useful according to other aspects of the invention in preventing cancer (e.g., reducing a risk of developing cancer) in a subject at risk of developing a cancer. A number of cancers are well known to those skilled in the art.

The disclosed nucleic acids may also be used for increasing the responsiveness of a cancer cell to a cancer therapy (e.g., an anti-cancer therapy), optionally when the proinflammatory nucleic acid is administered in conjunction with an anti-cancer therapy. The anti-cancer therapy may be a chemotherapeutic agent, a vaccine (e.g., an in vitro primed dendritic cell vaccine or a cancer antigen vaccine) or an antibody based therapy. This latter therapy may also involve administering an antibody specific for a cell surface antigen of, for example, a cancer cell, wherein the immune response results in antigen dependent cellular cytotoxicity (ADCC). Antibodies, natural and synthetic, related to cancer antigens are well known to those skilled in the art.

Thus, according to some aspects of the invention, a subject having cancer or at risk of having a cancer is administered a proinflammatory nucleic acid and an anti-cancer therapy. In some embodiments, the anti-cancer therapy is selected from the group consisting of a chemotherapeutic agent, an immunotherapeutic agent and a cancer vaccine. The proinflammatory nucleic acid may be co-administered, either simultaneously or during the same course of treatment, with interferon gamma. Cancer chemotherapeutic and immunotherapeutic agents are well known to those skilled in the art.

The invention in other aspects relates to methods for preventing disease in a subject. The method involves administering to the subject a proinflammatory nucleic acid on a regular basis to promote immune system responsiveness to prevent disease in the subject. Examples of diseases or conditions sought to be prevented using the prophylactic methods of the invention include microbial infections (e.g., sexually transmitted diseases) and anaphylactic shock from food allergies.

In other aspects, the invention is a method for inducing an innate immune response by administering to the subject a proinflammatory nucleic acid in an amount effective for activating an innate immune response.

Another method involves administering to a subject having or at risk of having a viral or retroviral infection, an effective amount for treating or preventing the viral or retroviral infection of any of the compositions of the invention. In some embodiments the virus is caused by a hepatitis virus, HIV, hepatitis B, hepatitis C, herpes virus, or papillomavirus.

Another aspect is a method involves administering to a subject having or at risk of having a bacterial infection or parasitic infection an effective amount for treating or preventing the bacterial infection or parasitic infection of any of the compositions of the invention. As the oligonucleotides of the instant invention are not necessarily species specific, the oligonucleotides may be used in animals as well as man.

In yet another aspect is a method for treating or preventing asthma and/or allergy, by administering to a subject having or at risk of having asthma and/or allergy, an effective amount for treating or preventing the asthma of any of the compositions of the invention. In one embodiment the asthma is allergic asthma. The compositions of the invention may be coadminstered, either simultaneously or in the same course of treatment, with other allergy and/or asthma medication. Such medications are well known to those skilled in the art.

Another method involves administering to a subject having or at risk of an immune deficiency, an effective amount of a composition of the instant invention for treating or preventing the immune deficiency.

Another aspect is a method for inducing a Th1 immune response by administering to a subject any of the compositions of the invention in an effective amount to produce a Th1 immune response, preferably without stimulating a Th2 response.

Another aspect, the disclosed proinflammatory nucleic acids are useful for not only their immune stimulatory properties but also in the treatment of bone and neural diseases as they are thought to act through the TREM pathways.

The disclosed proinflammatory nucleic acids are useful in some aspects of the invention as a prophylactic vaccine for the treatment of a subject at risk of developing an infection with an infectious organism or a cancer in which a specific cancer antigen has been identified or an allergy or asthma where the allergen or predisposition to asthma is known. Methods of identification of individuals at risk for allergy, asthma, or cancer; or having allergy, asthma, or cancer are well known to those skilled in the art.

The proinflammatory nucleic acids can also be given without the antigen or allergen for shorter term protection against infection, allergy or cancer, and in this case repeated doses will allow longer term protection. If the antigen is an allergen and the subject develops allergic responses to that particular antigen and the subject may be exposed to the antigen, i.e., during pollen season, then that subject is at risk of exposure to the antigen.

In addition to the use of the proinflammatory nucleic acids for prophylactic treatment, the invention also encompasses the use of the proinflammatory nucleic acids for the treatment of a subject having an infection, an allergy, asthma, or a cancer.

The proinflammatory nucleic acids can be used with an antigen to mount an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

The subject is exposed to the antigen. As used herein, the term exposed to refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the proinflammatory nucleic acid are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the proinflammatory nucleic acid. For instance, in a subject at risk of developing a cancer or an infectious disease or an allergic or asthmatic response, the subject may be administered the proinflammatory nucleic acid on a regular basis when that risk is greatest, i.e., during allergy season or after exposure to a cancer causing agent.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, Cancer Research, 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A microbial antigen as used herein is an antigen of a microorganism and includes but is not limited to virus (e.g., HIV, Picornavurudae, and Coronoviridae); bacteria (e.g., Gram negative and Gram positive bacteria); parasite; fungus (e.g., Chlamydia, Cryptococcus); and protist (e.g., Plasmodium, Leshmania). Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humeral and/or cellular) to a natural microorganism antigen. Such antigens are used routinely in the art and are well known to those of ordinary skill in the art. Other medically relevant microorganisms have been described extensively in the literature, e.g., see C. G. A Thomas, Medical Microbiology, Bailliere Tindall, Great Britain 1983, the entire contents of which is hereby incorporated by reference.

Although many of the microbial antigens described above relate to human disorders, the invention is also useful for treating other nonhuman vertebrates. Nonhuman vertebrates are also capable of developing infections which can be prevented or treated with the Proinflammatory nucleic acids disclosed herein. For instance, in addition to the treatment of infectious human diseases, the methods of the invention are useful for treating infections of animals. Many vaccines for the treatment of non-human vertebrates are disclosed in Bennett, K. Compendium of Veterinary Products, 3rd ed. North American Compendiums, Inc., 1995.

As used herein, the term treat, treated, or treating when used with respect to an infectious disease includes a prophylactic treatment which increases the resistance of a subject (a subject at risk of infection) to infection with a pathogen or, in other words, decreases the likelihood that the subject will become infected with the pathogen as well as a treatment after the subject (a subject who has been infected) has become infected in order to fight the infection, e.g., reduce or eliminate the infection or prevent it from becoming worse. Treatment can include administration of single or multiple doses of the compounds of the instant invention.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Allergens are well known to those skilled in the art.

The antigen may be an antigen that is encoded by a nucleic acid vector or it may be not encoded in a nucleic acid vector. In the former case the nucleic acid vector is administered to the subject and the antigen is expressed in vivo. In the latter case the antigen may be administered directly to the subject. An antigen not encoded in a nucleic acid vector as used herein refers to any type of antigen that is not a nucleic acid. For instance, in some aspects of the invention the antigen not encoded in a nucleic acid vector is a polypeptide. Minor modifications of the primary amino acid sequences of polypeptide antigens may also result in a polypeptide which has substantially equivalent antigenic activity as compared to the unmodified counterpart polypeptide. Such modifications may be deliberate, as by site-directed mutagenesis, or may be spontaneous. All of the polypeptides produced by these modifications are included herein as long as antigenicity still exists. The polypeptide may be, for example, a viral polypeptide.

The term substantially purified as used herein refers to a polypeptide which is substantially free of other proteins, lipids, carbohydrates or other materials with which it is naturally associated. One skilled in the art can purify viral or bacterial polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis. Other types of antigens not encoded by a nucleic acid vector such as polysaccharides, small molecule, mimics etc are described above, and included within the invention.

The invention also utilizes polynucleotides encoding the antigenic polypeptides. It is envisioned that the antigen may be delivered to the subject in a nucleic acid molecule which encodes for the antigen such that the antigen must be expressed in vivo. Such antigens delivered to the subject in a nucleic acid vector are referred to as antigens encoded by a nucleic acid vector. The nucleic acid encoding the antigen is operatively linked to a gene expression sequence which directs the expression of the antigen nucleic acid within a eukaryotic cell. The gene expression sequence is any regulatory nucleotide sequence, such as a promoter sequence or promoter-enhancer combination, which facilitates the efficient transcription and translation of the antigen nucleic acid to which it is operatively linked. The gene expression sequence may, for example, be a mammalian or viral promoter, such as a constitutive or inducible promoter. Such promoters are well known to those skilled in the art. The invention is not limited by the specific gene expression cassette used.

The antigen nucleic acid of the invention may be delivered to the immune system alone or in association with a vector. In its broadest sense, a vector is any vehicle capable of facilitating the transfer of the antigen nucleic acid to the cells of the immune system so that the antigen can be expressed and presented on the surface of the immune cell. The vector generally transports the nucleic acid to the immune cells with reduced degradation relative to the extent of degradation that would result in the absence of the vector. The vector optionally includes at least one gene expression sequence to enhance expression of the antigen nucleic acid in immune cells. In general, the vectors useful in the invention include, but are not limited to, plasmids, phagemids, viruses, other vehicles derived from viral or bacterial sources that have been manipulated by the insertion or incorporation of the antigen nucleic acid sequences. Such vectors are well known to those skilled in the art. The selection of a specific vector type is not a limitation of the instant invention.

Suitable viral vectors are based on non-cytopathic eukaryotic viruses in which non-essential genes have been replaced with the gene of interest. Such viruses are well known to those skilled in the art.

Other vectors include plasmid vectors. Plasmid vectors have been extensively described in the art and are well-known to those of skill in the art. See e.g., Sambrook et al., Molecular Cloning: A Laboratory Manual, Second Edition, Cold Spring Harbor Laboratory Press, 1989. Plasmids are commercially available and well-known to those of ordinary skill in the art. Additionally, plasmids may be custom designed using restriction enzymes and ligation reactions to remove and add specific fragments of DNA.

It has recently been discovered that gene carrying plasmids can be delivered to the immune system using bacteria. Modified forms of bacteria such as Salmonella can be transfected with the plasmid and used as delivery vehicles. The bacterial delivery vehicles can be administered to a host subject orally or by other administration means. The bacteria deliver the plasmid to immune cells, e.g. B cells, dendritic cells, likely by passing through the gut barrier. High levels of immune protection have been established using this methodology. Such methods of delivery are useful for the aspects of the invention utilizing systemic delivery of antigen, Proinflammatory nucleic acid and/or other therapeutic agent.

Thus, the proinflammatory nucleic acids are useful as vaccine adjuvants. It was previously established that CpG oligonucleotides are excellent vaccine adjuvants. It was also demonstrated, however, that CpG oligonucleotide which are superb vaccine adjuvants in mice are not the suitable adjuvants in non-rodent animals.

The proinflammatory nucleic acids can be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells.

Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites. Such agents are well known to those skilled in the art.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors. Such agents are well known to those skilled in the art.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleoside analogues), maturation of new virus proteins (e.g. protease inhibitors), and budding and release of the virus. Such agents are well known to those skilled in the art.

Anti-fungal agents are useful for the treatment and prevention of infective fungi. Anti-fungal agents are sometimes classified by their mechanism of action. Such agents are well known to those skilled in the art.

Proinflammatory nucleic acids can be combined with other therapeutic agents such as adjuvants to enhance immune responses. The proinflammatory nucleic acid and other therapeutic agent may be administered simultaneously or sequentially. When the other therapeutic agents are administered simultaneously they can be administered in the same or separate formulations, but are administered at the same time. The other therapeutic agents are administered sequentially with one another and with proinflammatory nucleic acid, when the administration of the other therapeutic agents and the proinflammatory nucleic acid is temporally separated. The separation in time between the administration of these compounds may be a matter of minutes or it may be longer. Other therapeutic agents include but are not limited to adjuvants, cytokines, antibodies, antigens, etc.

The proinflammatory nucleic acids are useful as adjuvants for inducing a systemic immune response. Thus, either can be delivered to a subject exposed to an antigen to produce an enhanced immune response to the antigen.

In addition to the proinflammatory nucleic acids, the compositions of the invention may also be administered with non-nucleic acid adjuvants. A non-nucleic acid adjuvant is any molecule or compound except for the proinflammatory nucleic acids described herein which can stimulate the humoral and/or cellular immune response. Non-nucleic acid adjuvants include, for instance, adjuvants that create a depo effect, immune stimulating adjuvants, and adjuvants that create a depo effect and stimulate the immune system. Such adjuvants are well known to those skilled in the art.

An immune stimulating adjuvant is an adjuvant that causes activation of a cell of the immune system. It may, for instance, cause an immune cell to produce and secrete cytokines. Such agents are well known to those skilled in the art.

The proinflammatory nucleic acids are also useful as mucosal adjuvants. It has previously been discovered that both systemic and mucosal immunity are induced by mucosal delivery of CpG nucleic acids. The systemic immunity induced in response to CpG nucleic acids included both humoral and cell-mediated responses to specific antigens that were not capable of inducing systemic immunity when administered alone to the mucosa. Furthermore, both CpG nucleic acids and cholera toxin (CT, a mucosal adjuvant that induces a Th2-like response) induced CTL. This was surprising since with systemic immunization, the presence of Th2-like antibodies is normally associated with a lack of CTL (Schirmbeck et al., 1995).

Mucosal adjuvants referred to as non-nucleic acid mucosal adjuvants may also be administered with the Proinflammatory nucleic acids. A non-nucleic acid mucosal adjuvant as used herein is an adjuvant other than an proinflammatory nucleic acid that is capable of inducing a mucosal immune response in a subject when administered to a mucosal surface in conjunction with an antigen. Such agents are well known to those skilled in the art.

Immune responses can also be induced or augmented by the co-administration or co-linear expression of cytokines (Bueler & Mulligan, 1996; Chow et al., 1997; Geissler et al., 1997; Iwasaki et al., 1997; Kim et al., 1997) or B-7 co-stimulatory molecules (Iwasaki et al., 1997; Tsuji et al., 1997) with the proinflammatory nucleic acids. The cytokines can be administered directly with proinflammatory nucleic acids or may be administered in the form of a nucleic acid vector that encodes the cytokine, such that the cytokine can be expressed in vivo. In one embodiment, the cytokine is administered in the form of a plasmid expression vector. The term cytokine is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-gamma (gamma-IFN), IFN-alpha, tumor necrosis factor (TNF), TGF-beta, FLT-3 ligand, and CD40 ligand.

Cytokines play a role in directing the T cell response. Helper (CD4+) T cells orchestrate the immune response of mammals through production of soluble factors that act on other immune system cells, including other T cells. Most mature CD4+ T helper cells express one of two cytokine profiles: Th1 or Th2. The Th1 subset promotes delayed-type hypersensitivity, cell-mediated immunity, and immunoglobulin class switching to $IgG_{2a}$. The Th2 subset induces humoral immunity by activating B cells, promoting antibody production, and inducing class switching to $IgG_1$ and IgE. In some embodiments, it is suitable that the cytokine be a Th1 cytokine.

The proinflammatory nucleic acids can also be administered in conjunction with an anti-cancer therapy. Anti-cancer therapies include cancer medicaments, radiation and surgical procedures. As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers. Treating cancer can require the administration of a single or multiple doses of the compound of the instant invention.

Additionally, the methods of the invention are intended to embrace the use of more than one cancer medicament along with the proinflammatory nucleic acids. As an example, where appropriate, the proinflammatory nucleic acids may be administered with a both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

Cancer medicaments function in a variety of ways. The methods of the invention are not limited by the cancer medicament or its mechanism of action.

The use of proinflammatory nucleic acids in conjunction with immunotherapeutic cancer medicaments such as monoclonal antibodies is able to increase long-term survival through a number of mechanisms including significant enhancement of ADCC (as discussed above), activation of natural killer (NK) cells and an increase in IFN-alpha levels. The nucleic acids when used in combination with monoclonal antibodies serve to reduce the dose of the antibody required to achieve a biological result.

Cancer vaccines are medicaments which are intended to stimulate an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells.

Although cancer vaccines may take one of several forms, as discussed infra, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. The use of proinflammatory nucleic acids in conjunction with cancer vaccines provides an improved antigen-specific humoral and cell mediated immune response, in addition to activating NK cells and endogenous dendritic cells, and increasing IFN-alpha levels. This enhancement allows a vaccine with a reduced antigen dose to be used to achieve the same beneficial effect. In some instances, cancer vaccines may be used along with adjuvants, such as those described above.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Other vaccines take the form of dendritic cells which have been exposed to cancer antigens in vitro, have processed the antigens and are able to express the cancer antigens at their cell surface in the context of MHC molecules for effective antigen presentation to other immune system cells.

As used herein, chemotherapeutic agents embrace all other forms of cancer medicaments which do not fall into the categories of immunotherapeutic agents or cancer vaccines. Chemotherapeutic agents as used herein encompass both chemical and biological agents and act by a number of mechanisms, both known and unknown. The mechanism of action of these agents is not a limitation of the invention.

In one embodiment, proinflammatory nucleic acids are used as a replacement to the use of IFN-alpha therapy in the treatment of cancer. Currently, some treatment protocols call for the use of IFN-alpha. Since IFN-alpha is produced following the administration of some proinflammatory nucleic acids, these nucleic acids can be used to generate IFN-alpha endogenously.

A further embodiment includes a method for inducing antigen non-specific innate immune activation and broad spectrum resistance to infectious challenge using the proinflammatory nucleic acids. The term antigen non-specific innate immune activation as used herein refers to the activation of immune cells other than B cells and for instance can include the activation of NK cells, T cells or other immune cells that can respond in an antigen independent fashion or some combination of these cells. A broad spectrum resistance to infectious challenge is induced because the immune cells are in active form and are primed to respond to any invading compound or microorganism. The cells do not have to be specifically primed against a particular antigen. This is particularly useful in biowarfare, and the other circumstances such as for travelers going to areas with high incidence of infectious disease.

The proinflammatory nucleic acids may be directly administered to the subject or may be administered in conjunction with a nucleic acid delivery complex. A nucleic acid delivery complex shall mean a nucleic acid molecule associated with (e.g. ionically or covalently bound to; or encapsulated within) a targeting means (e.g. a molecule that results in higher affinity binding to target cell (e.g., B cell surfaces and/or increased cellular uptake by target cells). Examples of nucleic acid delivery complexes include nucleic acids associated with a sterol (e.g. cholesterol), a lipid (e.g. a cationic lipid, virosome or liposome), or a target cell specific binding agent (e.g. a ligand recognized by target cell specific receptor). Suitable complexes may be sufficiently stable in vivo to prevent significant uncoupling prior to internalization by the target cell. However, the complex can be cleavable under appropriate conditions within the cell so that the nucleic acid is released in a functional form.

Delivery vehicles or delivery devices for delivering antigen and nucleic acids to surfaces have been described and are well known to those skilled in the art. Some examples are provided below in the discussion of vectors.

The term "effective amount of a proinflammatory nucleic acid" refers to the amount necessary or sufficient to realize a desired biologic effect. For example, an effective amount of a proinflammatory nucleic acid for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and suitable mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular proinflammatory nucleic acid being administered, the antigen, the size of the subject, or the severity of the disease or condition. One of ordinary skill in the art can empirically determine the effective amount of a particular proinflammatory nucleic acid and/or antigen and/or other therapeutic agent without necessitating undue experimentation.

Subject doses of the compounds described herein for mucosal or local delivery typically range from about 0.1 ug to 10 mg per administration, which depending on the application could be given daily, weekly, or monthly and any other amount of time there between. However, dosing may be at substantially higher or lower ranges. Determination of appropriate dosing ranges and frequency is well within the ability of those skilled in the art.

For any compound described herein the therapeutically effective amount can be initially determined from animal models. A therapeutically effective dose can also be determined from human data for CpG oligonucleotides which have been tested in humans (human clinical trials have been initiated) and for compounds which are known to exhibit similar pharmacological activities, such as other mucosal adjuvants, e.g., LT and other antigens for vaccination purposes, for the mucosal or local administration. Higher doses are required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the proinflammatory nucleic acid can be administered to a subject by any mode that delivers the nucleic acid to the desired surface, e.g., mucosal, systemic. Administering the pharmaceutical composition of the present invention may be accomplished by any means known to the skilled artisan. Suitable routes of administration include but are not limited to oral, parenteral, intramuscular, intranasal, intratracheal, inhalation, ocular, vaginal, and rectal. Such formulations are well known by those skilled in the art, as are considerations for optimal dosing routes.

The proinflammatory nucleic acids and optionally other therapeutics and/or antigens may be administered per se (neat) or in the form of a pharmaceutically acceptable salt. Such salts are well known to those skilled in the art.

The pharmaceutical compositions of the invention contain an effective amount of an Proinflammatory nucleic acid and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The proinflammatory nucleic acids useful in the invention may be delivered in mixtures with additional adjuvant(s), other therapeutics, or antigen(s). A mixture may consist of several adjuvants in addition to the proinflammatory nucleic acid or several antigens or other therapeutics.

A variety of administration routes are available. The particular mode selected will depend, of course, upon the particular adjuvants or antigen selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Suitable modes of administration are well known to those skilled in the art.

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories. For treatment of a patient, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units. Multiple administrations of doses at specific intervals of weeks or months apart is usual for boosting the antigen-specific responses.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. In addition, pump-based hardware delivery systems can be used, some of which are adapted for implantation.

The proinflammatory nucleic acids can be any length. The proinflammatory nucleic acids can comprise from about 8 to about 80 nucleobases (i.e. from about 8 to about 80 linked nucleosides). Consequently, the proinflammatory nucleic acids disclosed herein comprise at lease 8 contiguous monomer units. One of ordinary skill in the art will appreciate that the invention embodies these compounds can have 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases. The proinflammatory nucleic acids can be single stranded or double stranded.

The terms "nucleic acid" and "oligonucleotide" are used interchangeably to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). As used herein, the terms refer to oligoribonucleotides as well as oligodeoxyribonucleotides. The terms shall also include polynucleosides (i.e. a polynucleotide minus the phosphate) and any other organic base containing polymer. Nucleic acid molecules can be obtained from existing nucleic acid sources (e.g., genomic or cDNA), but are preferably synthetic (e.g. produced by nucleic acid synthesis).

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound; however branched structures are known in the art. Optionally, the respective ends of this linear polymeric compound can be further joined to form a circular compound. Also, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Oligomeric compounds can include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Suitable modified oligonucleotide backbones containing a phosphorus atom therein include, for example, phosphorothioates, chiral phosphorothioates, phosphorodithioates, phosphotriesters, aminoalkylphosphotriaminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3',5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, including sodium and potassium salts, as well as mixed salts and free acid forms, are also included herein.

Suitable modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Modified Sugar and Internucleoside Linkages-Mimetics

In other oligomeric compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Some embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Other embodiments are oligonucleotides having morpholino backbone structures of the above-referenced U.S. Pat. No. 5,034,506.

Modified Sugars

Modified oligomeric compounds can also contain one or more substituted sugar moieties. Oligomeric compounds can contain one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Such 2' position substitutions can be selected from the group: $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_n$ ON[(CH$_2$)$_n$CH$_3$]$_2$, where n and m are from 1 to about 10. Other suitable oligomeric compounds comprise one of the following at the 2' position: C1 to C10 lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Modifications can include 2'-methoxyethoxy (2'-O—CH$_2$CH$_2$OCH$_3$, also known as 2'-O-(2-methoxyethyl) or 2'-MOE) (Martin et al., Hely. Chim. Acta, 1995, 78, 486-504) i.e., an alkoxyalkoxy group. Another suitable modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples hereinbelow.

Other suitable modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), (2'-O—CH$_2$—CH=CH$_2$) and 2'-fluoro (2'-F). The 2'-modification can be in the arabino (up) position or ribo (down) position. One such 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligomeric compounds can also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Another modification of the sugar includes Locked Nucleic Acids (LNAs) in which the 2'-hydroxyl group is linked to the 3' or 4' carbon atom of the sugar ring, thereby forming a bicyclic sugar moiety. The linkage can be a methylene (—CH2-)n group bridging the 2' oxygen atom and the 4' carbon atom wherein n is 1 or 2. LNAs and preparation thereof are described in WO 98/39352 and WO 99/14226.

Natural and Modified Nucleobases

Oligomeric compounds can also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include but are not limited to other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2($^3$H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases can also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of the oligomeric compounds. These include but are not limited to 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750, 692, which is commonly owned with the instant application and also herein incorporated by reference.

Conjugates

Another modification of the oligomeric compounds involves chemically linking to the oligomeric compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance pharmacokinetic properties include groups that improve uptake, distribution, metabolism or excretion of the oligomeric compounds. Representative conjugate groups are disclosed in International Patent Application PCT/US92/09196, filed Oct. 23, 1992, and U.S. Pat. No. 6,287,860, the entire disclosure of which is incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligomeric compounds can also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

"Chimeric" oligomeric compounds or "chimeras," which contain two or more chemically distinct regions, each made up of at least one monomer unit, e.g., a nucleotide in the case of an oligonucleotide compound. Oligonucleotides exemplified herein include "gapmers". As used in the present invention the term "gapmer" refers to an oligomeric compound comprising a contiguous sequence of nucleosides that is divided into 3 regions, an internal region (gap) flanked by two external regions (wings). The regions are differentiated from each other at least by having differentially modified sugar groups that comprise the nucleosides. In some embodiments, each modified region is uniformly modified (e.g. the modified sugar groups in a given region are identical); however, other motifs can be applied to regions. For example, the wings in a gapmer could have an alternating motif. The internal region or the gap may, in some instances, comprise uniform unmodified β-D-ribonucleosides or β-D-deoxyribonucleosides or can be a sequence of nucleosides having uniformly modified sugars. The nucleosides located in the gap of a gapped oligomeric compound have sugar moieties that are different than the modified sugar moieties in each of the wings. Oligonucleotides disclosed herein include "MOE-gapmers" which have 2'-MOE modifications in the wings, full PS backbones, and frequently 5'MeC modifications on all of the cytosines.

Chimeric oligomeric compounds can be formed as composite structures of two or more oligomer compounds such as oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Each of the limitations of the invention can encompass various embodiments of the invention. It is, therefore, anticipated that each of the limitations of the invention involving any one element or combinations of elements can be included in each aspect of the invention.

EXAMPLES

Example 1

Nucleoside Phosphoramidites for Oligonucleotide Synthesis-Deoxy and 2'-alkoxy amidites Methods of synthesis of phosphoramidites, including those with 2'-, 3'- and 5'-modifications, are well known to those skilled in the art. Moreover, the method of synthesis of phosphoramidites is not a limitation of the instant invention.

Example 2

Oligonucleotide Synthesis

Methods of synthesis of oligonucleotides, including those with 2'-, 3'- and 5'-modifications, modified backbones, and/or nucleobase analogs (e.g., PNA) are well known to those skilled in the art. Moreover, the method of synthesis of oligonucleotides is not a limitation of the instant invention.

Example 3

Oligonucleotide Isolation

Oligonucleotides of the instant invention are preferably isolated by HPLC. However, other methods of oligonucleotide isolation are known to those skilled in the art, and method of oligonucleotide isolation is not a limitation of the instant invention.

Example 4

Oligonucleotide Synthesis and Analysis-96 Well Plate Format

Oligonucleotide synthesis and analysis are preferably carried out using solid phase synthesis and capillary gel electrophoresis methods in a standard 96-well plate format. Such methods are well known to those skilled in the art. However, the method of oligonucleotide synthesis is not a limitation of the instant invention.

Example 5

Antisense Oligonucleotide-mediated Proinflammatory Studies

In accordance with the present invention, studies in TLR9 (−/−) and Myd88 (−/−) knockout mice were performed to determine the TLR dependence of the proinflammatory effects of certain antisense oligonucleotides. Studies using TLR9(−/−) knockout mice were performed as per the methods of Hemmi (Hemmi et al; 2000, Nature; 408, 740-745) herein incorporated by reference in its entirety.

TLR9 knockout mice and C57BL6 (wild type) mice were treated with a CpG Optimal oligonucleotide (ISIS-12449), a phosphorothioate oligonucleotide (ISIS-2105), a 2′MOE oligonucleotide (ISIS-116847), or phosphate buffered saline (PBS) as a control. Animals were dosed twice a week for three weeks. At the end of the study, animals were sacrificed and evaluated for organ weight (liver and spleen), serum chemistry, tissue histology, mRNA and protein levels (liver and spleen) and isolated bone marrow cells were harvested for further analysis. The sequences tested and the resulting data are shown in the following Tables.

TABLE 2

Determination of TLR9 dependence of oligonucleotide treatment

| | Fold increase in spleen weight | |
|---|---|---|
| ISIS Number | TLR9 knockout mice | Wild type mice |
| Saline | 1.0 | 1.0 |
| 12449; 4 mg/kg | 1.2 | 4.8 |
| 2105; 20 mg/kg | 1.4 | 1.5 |
| 2105; 50 mg/kg | 1.6 | 2.0 |
| 116847; 20 mg/kg | 1.0 | 1.1 |
| 116847; 50 mg/kg | 1.5 | 1.3 |

These data demonstrate that the CpG oligonucleotide (12449) acts via TLR9 to promote an inflammatory response as spleen weight is substantially increased in the wild type mice as compared to the knockout mice. The non-CpG oligonucleotides of the instant invention act via a TLR9 independent pathway as the increase in spleen weight observed in the wild type and TLR9 knockout animals are comparable for each of the doses of each of the two oligonucleotides.

TABLE 1

Oligonucleotide sequences and chemistries

| Sequence Type | Isis Number | SEQ ID NO: | Sequence; 5'-3'/chemistry |
|---|---|---|---|
| CpG Optimal phosphorothioate | 12449 | 1 | ACCGATAACGTTGCCGGTGACG/full phosphorothioate and full 2'deoxy sugars. |
| PS-ODN | 148523 | 2 | ACCTCCTCCATGGCTCTTCT/5-10-5 MOE gapmer, phosphorothioate backbone with 5-methy cytosines. |
| PS-ODN | 219556 | 3 | CTAAGTCACCTTGTTGCCAT/5-10-5 MOE gapmer, phosphorothioate backbone with 5-methy cytosines. |
| PS-ODN | 2105 | 4 | TTGCTTCCATCTTCCTCGTC/5-10-5 MOE gapmer, phosphorothioate backbone with 5-methy cytosines. |
| Inflammatory 2'MOE non-CpG Listed from least to most inflammatory | 141923 (least inflammatory) | 5 | CCTTCCCTGAAGGTTCCTCC/5-10-5 MOE gapmer, phosphorothioate backbone with 5-methy cytosines. |
| Inflammatory 2'MOE non-CpG | 113131 | 6 | CGTGTGTCTGTGCTAGTCCC/5-10-5 MOE gapmer, phosphorothioate backbone with 5-methy cytosines. |
| Inflammatory 2'MOE non-CpG | 116847 | 7 | CTGCTAGCCTCTGGATTTGA/5-10-5 MOE gapmer, phosphorothioate backbone with 5-methy cytosines. |
| Inflammatory 2'MOE non-CpG | 129605 | 8 | CCTGCTCCCTCTAATGCTGC/5-10-5 MOE gapmer, phosphorothioate backbone with 5-methy cytosines. |
| Inflammatory 2'MOE non-CpG | 128427 | 9 | CGCAACCTCCGCCAGCCGTC/5-10-5 MOE gapmer, phosphorothioate backbone with 5-methy cytosines. |
| Inflammatory 2'MOE non-CpG | 147420 (most inflammatory) | 10 | AATGTGCCTGCTGTCCTTGA/5-10-5 MOE gapmer, phosphorothioate backbone with 5-methy cytosines. |
| Inflammatory with simple repeat | 263926 | 11 | CTCCCTCTCTCCCTCTCTCT/5-10-5 MOE gapmer, phosphorothioate backbone with 5-methy cytosines. |

TABLE 3 mRNA expression of innate immune response genes in whole liver

| Treatment | Fold increase in expression of immune response gene | | | | |
|---|---|---|---|---|---|
| | MIP2 | IFN-gamma | IL-12 | IL-18 | GRO-1 |
| Saline Wild type | 1.0 | 1.0 | 1.0 | 1.0 | 1.0 |
| Saline TLR9 (−/−) mice | 1.0 | 1.0 | 1.0 | 1.0 | 1.0 |
| 12449; Wild type | 5.5 | >15 | >15 | >15 | 3 |
| 12449; TLR9 (−/−) mice | 1.2 | N.D | 2 | 9.5 | N.D. |
| 116847; wild type | 6 | 2.5 | 13 | 2.5 | 2.6 |
| 116847; TLR9 (−/−) mice | 7 | 1.0 | 7 | 3.5 | 1.5 |

N.D. means not determined.

The data further demonstrate the TLR9 dependence of the CpG oligonucleotides to produce an inflammatory response. The level of MIP2, IL-12 and IL-18 are substantially increased in the wild type animals as compared to the TLR9 knockout animals for the TLR9 dependent oligonucleotides. All inflammatory reponse genes are substantially increased in CpG oligonucleotide treated animals relative to wild-type and TLR 9 saline treated animals. The non-CpG proinflammatory oligonucleotide of the instant invention increased the expression of MIP2 and IL-18 to a comparable level in both wild type and TLR9 knockout mice, and increased IL-12 and GRO-1 substantially as compared to saline treated control mice.

TABLE 4 mRNA expression of cell surface markers in whole liver

| Treatment | Fold increase in expression of cell surface marker | | | |
|---|---|---|---|---|
| | CD11b | CD11c | TLR9 | CD86 |
| Saline Wild type | 1.0 | 1.0 | 1.0 | 1.0 |
| Saline TLR9 (−/−) mice | 1.0 | 1.0 | 1.0 | 1.0 |
| 12449; Wild type | 10.5 | >15 | 8.5 | 7 |
| 12449; TLR9 (−/−) mice | 1 | 1 | 1 | 1.5 |
| 116847; wild type | 2 | 5 | 2.5 | 1.5 |
| 116847; TLR9(−/−) mice | 2 | 2.5 | 1 | 2 |

Again, the results further demonstrate that TLR9 is not required for a proinflammatory effect by the non-CpG oligonucleotides of the instant invention.

TABLE 5

2'MOE antisense oligonucleotides exhibit sequence dependent proinflammatory responses

| Treatment | Fold increase in expression of immune response genes | |
|---|---|---|
| | MIP-2 | CD86 |
| Saline Wild type | 1.0 | 1.0 |
| Saline TLR9 mice | 1.0 | 1.0 |
| 12449; Wild type | 1.8 | 1.5 |
| 12449; TLR9 mice | 1.4 | 1.5 |
| 116847; wild type | 6 | 1.5 |
| 116847; TLR9 mice | 7 | 2.5 |
| 148523; wild type | >10 | 3 |
| 148523; TLR9 mice | >10 | 4 |

The ISIS 148523, a 5-10-5 MOE-gapmer, provides a further example of a non-CpG oligonucleotide that promotes TLR9-independent immunostimulation.

Example 6

Expression of TREM and NOD Receptors in Treated Mouse Liver

A number of possible receptors for non-CpG proinflammatory oligonucleotides were proposed. Two families of potential receptors were analyzed, the CARD and TREM families. The CARD family comprises roughly 20 intracellular proteins and contain a leucine rich repeat domain and a caspase recruitment domain. Members include NOD1 and NOD2 which are activated by bacterial components and are induce NFkB activation.

The members of the TREM family are transmembrane proteins that have a small intracellular domain and an Ig like repeat in the extracellular domain. There are at least 4 TREM receptors and several TREM like inhibitory molecules.

TREM-1 has been shown to enhance LPS signaling and addition of soluble TREM-1 prevents LPS-induced shock. TREM-2 has been shown to bind large anionic molecules. Wild type and knockout mice were treated with oligonucleotides of the present invention and levels of TREM and NOD receptors were measured in treated mouse livers. These data are in Table 6.

TABLE 6

Receptor expression in treated mouse liver; in vivo studies

| Treatment | Relative Fold increase in expression | | |
|---|---|---|---|
| | CARD4 (NOD1) | CARD15 (NOD2) | TREM-2 |
| Saline WT | 1 | 1 | 1 |
| Saline TLR9 knockout | 1.5 | 2 | 1 |
| 12449 WT | 6 | 13 | 4 |
| 12449 TLR9 knockout | 1.5 | 3 | 2 |
| 116847 WT | 1 | 3 | >25 |
| 116847 TLR9 knockout | 2 | 5 | >25 |

These data demonstrate a moderate increase in the expression of CARD15 and a substantial increase in the expression of TREM-2 in response to treatement with the proinflammatory oligonucleotides of the instant invention in both wild type and TLR9 knockout mice. No corresponding increase is observed in liver in mice treated with the CpG proinflammatory oligonucleotide. This strongly suggests a role for TREM-2 in mediating the inflammatory response to proinflammatory non-CpG oligonucleotides.

Example 7

Myeloid Cell Response to Oligonucleotide Exposure

In order to examine a tissue traditionally involved in the innate immune response, bone marrow was isolated from wild type, TLR9(−/−), and Myd88(−/−) knockout mice. Cells were cultured and treated with 100 ug/mL of CpG optimal oligonucleotide, PS-ODN, and 2'MOE ASOs. Production of cytokines and chemokines were measured.

TABLE 7

MIP-2 Cytokine/chemokine production

| Treatment | Fold increase in expression MIP-2 | |
|---|---|---|
| | Wild type | TLR9(−/−) |
| Saline | 1.0 | 1.0 |
| 12449 | 7.5 | 2 |

TABLE 7-continued

MIP-2 Cytokine/chemokine production

| | Fold increase in expression MIP-2 | |
|---|---|---|
| Treatment | Wild type | TLR9(−/−) |
| 116847 | 1.8 | 2.3 |
| 2105 | 1.5 | 2.5 |

The results demonstrate that isolated bone marrow is predictive of proinflammatory activity of oligonucleotides, and their TLR9 dependence. The non-CpG oligonucleotides resulted in comparable immunostimulation as measured by MIP-2 production in bone marrow from wild type and TLR9 knockout animals. Stimulation of MIP-2 secretion by the CpG oliognucleotide was substantially decreased in the TLR9 knockout animals.

Example 8

Kinetics of Activation of the MAPK Pathway by Immunostimulatory Oligonucleotides ISIS-12449 was tested for its ability to activate ERK 1/2 in the bone marrow cells of both wild type, TLR9, and Myd88 knockout mice. This activation was determined to occur on a different time course than with CpG optimal oligonucleotides which show an increased activation demonstrated 15 minutes after treatment, as opposed to stimulation by a 2'MOE oligonucleotide which showed induction at 60 minutes.

Kinetics of activation of JNK, another member of the MAPK family, was reversed relative to activation of the ERKs. Onset of JNK expression with the CpG optimal oligonucleotide was observed at 30 minutes, wherein stimulation by the 2'MOE oligonucleotide was observed at 5 minutes.

Kinetics of activation of a third gene in the MAPK pathway, p38, showed onset of expression with the CpG optimal oligonucleotide occurring at 15 minutes and the 2'MOE oligonucleotide at 5 minutes, but then tapering off.

Example 9

Characterization of Raw 264.7 Cells for Examining Proinflammatory Properties

RAW 264.7 cells are a mouse macrophage cell line established from a tumor induced in a male mouse by intraperitoneal injection of Abelson Leukemia Virus (A-MuLV) (Raschkea et al., Cell. 15:261-267.1978) were used. The cells are capable of antibody dependent lysis of sheep erythrocytes and tumor targets. They express a number of TLRs and alternate immune system receptors.

Cells were tested for the ability to produce cytokines in response to proinflammatory oligonucleotides at a concentration of 100 ug/ml. The data are presented below.

TABLE 8

TNF-alpha production in cells when stimulated

| | TNFalpha production in pg/ml | | |
|---|---|---|---|
| Treatment | GM-CSF | GM/IL-4 | M-CSF |
| Saline | 1.0 | 1.0 | 1.0 |
| 141923 | 15 | 25 | N.D. |
| 129605 | 2 | 15 | N.D. |
| 147420 | 50 | 5 | N.D. |
| 219556 | 7 | 15 | N.D. |
| 12449 | 40 | 2 | 18 |

These data demonstrate distinct activation patterns of cytokines between CpG and non-CpG proinflammatory oligonucleotides. MIP-2 production was also increased in response to treatment with both proinflammatory oligonucleotides.

RAW 264.7 cells were also analyzed for the upregulation of cell surface receptors TREM-2 and TREM-3 in response to proinflammatory oligonucleotides.

TABLE 9

Receptor expression in treated cells; in vitro studies

| | Relative Fold increase in expression | |
|---|---|---|
| Treatment | TREM-2 | TREM-3 |
| Saline | 1 | 1 |
| 12449 | 0.5 | 4.5 |
| 116847 | 1 | 5 |
| 219556 | 2.5 | 4.5 |

A specific upregulation of expression of TREM-2 was observed in RAW 264.7 cells in response to treatment with ISIS 219556. TREM-3 expression was increased in response to all of the proinflammatory oligonucleotides tested.

RAW 264.7 cells were used to analyze the kinetics of activation of MAPKs in response to various oligonucleotides. As with bone marrow cells, the kinetics of activation of ERK1/2 were slower in response to ISIS 116847 as compared to ISIS 12449. ISIS 116487 was shown to stimulate tyrosine phosphorylation of intracellular proteins, specifically ZAP-70/Syk which is known to be involved in TREM signaling. A 1000-fold higher dose was required to stimulate ZAP-70/Syk phosphorylation using the CpG optimized oligonucleotide. Treatment of cells with bafilomycin which inhibits receptor internalization was found to inhibit ISIS 12449 signaling, but did not affect ISIS 116847 signaling.

These data further confirm that the non-CpG oligonucleotides of the instant invention signal through a distinct pathway from CpG oligonucleotides, and that RAW 264.7 cells mimic bone marrow in response to proinflammatory oligonucleotides.

Example 10

Characterization of Receptor Dependent Activation in Raw 264.7 Cells

Having established that RAW 264.7 respond to proinflammatory oligonucleotides by increasing cytokine production, an analysis was performed to identify the receptor through which the non-CpG oligonucleotide signaling was mediated.

RAW 264.7 cells were treated with siRNAs targeted to TREM-1, TREM-2, TLR-3 and TLR-7 to inhibit expression of the target genes prior to stimulation with ISIS121907 (5'-ACCGATAACGTTGCCGGTGACG-3' (SEQ ID NO: 12), 6-10-6 MOE-gapmer with 5-MeC, phosphorothioate backbone), 116487, or 219556 at 100 ug/ml. Treatment of cells with siRNAs targeted to TREM-7 or TREM-1 had little or no effect on MIP-2 production, respectively. siRNAs targeted to TREM-2 or TLR-3 decreased MIP-2 production with siRNA targeted to TREM-2 having the greatest effect on stimulation by ISIS 116847 and the siRNA targeted to TLR-3 having the greatest effect on ISIS 219556.

siRNAs targeted to TREM-1, TREM-2, and TLR-7 all decreased the production of TNF-alpha, with the greatest effect on stimulation by ISIS 116487. A decrease in TNF-alpha expression was also observed in stimulation by ISIS 121907 and 219556. siRNA targeted to TLR-3 did not decrease production of TNF-alpha in response to the proinflammatory oligonucleotides.

Example 11

Analysis of Receptor Dependent Activation to Proinflammatory Oligonucleotides in Mice To confirm the role of TREM-2 in mediating the response to non-CpG proinflammatory oligonucleotides, mice were treated with PBS (vehicle control) or an oligonucleotide targeted to TREM-2 (ISIS 219208, 5'-GCCCAGCATCTTG-GCCACAG-3' (SEQ ID NO: 13) 5-10-5 MOE-gapmer with 5-MeC, phosphorothioate backbone) at 100 mg/kg/week for two weeks to decrease expression of TREM-2 (n=5 per group). Animals were challenged with a single dose of 50 mg/kg ISIS 141923 or 147420 by subcutaneous (s.c.) injection. Animals were sacrificed three days post-challenge. Liver, spleen, and blood were collected. Cytokine profiling and TREM-2 expression were analyzed in liver. Expression of TREM-2 was decreased slightly upon treatment with the antisense oligonucleotide targeted to TREM-2. Expression of TREM-2 was increased slightly in response to treatment with ISIS 141923 in untreated animals. Treatment with ISIS 147420 or a combination of 147420 and 141923 resulted in about a 2-fold increase in expression of TREM-2. Challenge with ISIS 147420 after treatment with the oligonucleotide targeted to TREM-2 also resulted in about a two-fold increase over the expression level of TREM-2 in the antisense oligonucleotide treated, unchallenged animals.

Similar results were seen in the cytokine expression analysis. Treatment with ISIS 141923 or 219208 had little effect on cytokine signaling. Treatment with ISIS 147420 or a combination of 147420 and 141923 resulted in a small increase in IL-1alpha expression, a moderate increase in MCP-1 expression, and a large increase in MIP-1a and MCP5 expression. Treatment with the antisense oligonucleotide targeted TREM-2 prior to ISIS 147420 challenge, dampened, but did not eliminate, cytokine induction.

These data demonstrate that an oligonucleotide targeted to TREM-2 can decrease target expression in the liver. Moreover, challenge with a proinflammatory oligonucleotide can increase the expression of TREM-2 in the liver. Furthermore, a decrease of TREM-2 expression dampens oligonucleotide-induced cytokine and chemokine production.

Example 12

Development of an In Vitro Screening System Using a TREM2-chimera

Having established a critical role for TREM-2 in signaling of non-CpG proinflammatory oligonucleotides, an in vitro assay was established to facilitate screening of oligonucleotides for proinflammatory activity via a TREM-2 dependent pathway.

RAW 264.7 cells were transiently transfected with mouse TREM-2 or TREM-3 and the NFAT-SEAP reporter construct described above. Cells were subsequently treated with 1 ug/ml of saline, or the proinflammatory oligonucleotides ISIS 12449, or ISIS 219556. Production of SEAP was measured using a commercially available SEAP kit (Clontech Laboratories, Inc.). RAW 264.7 cells expression NFAT-SEAP reporter alone exhibited no detectable increase in SEAP production in response to treatment with saline, ISIS 12449, or ISIS 219556. RAW 264.7 cells overexpressing TREM-2 exhibited a 14-fold increase in NFAT-driven SEAP production in response to treatment with either ISIS 12449 or ISIS 219556. No increase in SEAP production was seen in response to treatment with the proinflammatory oligonucleotides in cells overexpressing TREM-3 containing the reporter construct. These data demonstrate that the proinflammatory oligonucleotides are functioning through TREM-2.

RAW 264.7 cells were transiently transfected with the TREM-2 chimera and treated with 100 ug/ml of Poly dI:dC, ISIS 263926, ISIS 148523, or saline for 2 hours. Nuclear protein was isolated, normalized, and assayed for NFAT activity by ELISA. Relative fold activation of NFAT was greater that 17-fold in the presence of the TREM-2 chimera and either ISIS 263926 or ISIS 148523, the proinflammatory oligonucleotides. The chimera expressing cells exhibited a minimal decrease in NFAT DNA binding as analyzed by ELISA, in the presence of Poly dI:dC, a compound of similar chemical nature to the oligonucleotides.

RAW 264.7 cells were treated with 1 ug/ml of ISIS 12449, 116847 or 219556, and the media was assayed for the presence of SEAP. Treatment with ISIS 12249 had no effect on SEAP expression as compared to PBS treated cells. Treatment of cells with ISIS 116847 or 219556 resulted in greater than two fold increase of SEAP expression as compared to PBS or ISIS 12249 treatment. Treatment of cells expressing only the NAFT reporter construct produced less than a 0.25 fold effect on expression of SEAP. These data demonstrate the substantial effect of the proinflammatory effects of the oligonucleotides of the instant invention, and that their activity is mediated via TREM-2.

RaAW 264.7 cells were transiently transfected with mouse TREM-2 or TREM-3 and the NFAT-SEAP reporter construct described above. Cells were subsequently treated with 1 ug/ml of saline, or the proinflammatory oligonucleotides ISIS 12449, or ISIS 219556. Production of SEAP was measured using a commercially available SEAP kit (Clontech Laboratories, Inc.). RAW 264.7 cells expression NFAT-SEAP reporter alone exhibited no detectable increase in SEAP production in response to treatment with saline, ISIS 12449, or ISIS 219556. RAW 264.7 cells overexpressing TREM-2 exhibited a 14-fold increase in NFAT-driven SEAP production in response to treatment with either ISIS 12449 or ISIS 219556. No increase in SEAP production was seen in response to treatment with the proinflammatory oligonucleotides in cells overexpressing TREM-3 containing the reporter construct. These data demonstrate that the proinflammatory oligonucleotides are functioning through TREM-2.

These data demonstrate that the screening method of the instant invention is sensitive and specific for the detection of proinflammatory oligonucleotides that act via the TREM-2 receptor. The method can be used as a positive selection for oligonucleotides to be used for proinflammatory purposes, or as a negative selection method for oligonucleotides to be used in situations where immune stimulation is not desired.

What is claimed is:

1. A method for identifying a proinflammatory oligonucleotide comprising:

contacting a cell with a test oligonucleotide wherein:

the cell functionally expresses a TREM-2 extracellular domain, an intracellular signaling domain, and a reporter construct comprising a cis-acting DNA consensus element sensitive to activation of the intracellular domain, and wherein the cis-acting DNA consensus element is functionally linked to a reporter gene coding sequence; and wherein the test oligonucleotide does not comprise a CpG motif, and wherein the oligonucleotide does not specifically hybridizes to a nucleic acid encoding TREM-2;

assaying for activation of the reporter gene; and identifying test oligonucleotide as being proinflammatory if the reporter gene is activated.

2. The method of claim 1, wherein the cell is a RAW 264.7 cell.

3. The method of claim 1, wherein the intracellular signaling domain activates transcription factor nuclear factor of activated T cells (NFAT).

4. The method of claim 1, wherein the intracellular signaling domain directly activates a transcription factor.

5. The method of claim 1, wherein the intracellular signaling domain indirectly activates a transcription factor.

6. The method of claim 1, wherein the cis-acting DNA consensus element is a transcription factor binding site.

7. The method of claim 6, wherein the transcription factor binding site is an NFAT binding site.

8. The method of claim 1, wherein the reporter gene is selected from the group consisting of beta-galactosidase, beta-lactamase, luciferase, and alkaline phosphatase.

9. The method of claim 1, wherein the reporter gene is secreted alkaline phosphatase.

10. The method of claim 1, wherein the intracellular signaling domain comprises a TREM-2 intracellular signaling domain.

11. The method of claim 1, wherein the intracellular signaling domain comprises a CD3ζ cytoplasmic domain.

12. The method of claim 1, wherein the test oligonucleotide consists of a single-stranded modified antisense oligonucleotide.

13. The method of claim 12, wherein at least one internucleoside linkage of the single-stranded modified antisense oligonucleotide is a modified internucleoside linkage.

14. The method of claim 13, wherein each internucleoside linkage of the single-stranded modified antisense oligonucleotide is a phosphorothioate internucleoside linkage.

15. The method of claim 12, wherein the single-stranded modified antisense oligonucleotide comprises at least one modified sugar moiety.

16. The method of claim 15, wherein at least one modified sugar moiety comprises a 2'-O-methoxyethyl or a 4'-$(CH_2)_n$—O-2' bridge, wherein n is 1 or 2.

17. The method of claim 12, wherein at least one nucleoside comprises a modified nucleobase.

18. The method of claim 17, wherein the modified nucleobase is a 5-methylcytosine.

19. The method of claim 1, wherein the test oligonucleotide comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar.

20. The method of claim 19, wherein the test oligonucleotide comprises:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment, wherein each nucleoside of each wing segment comprises a 2'-O-methoxyethyl sugar; wherein each cytosine in the test oligonucleotide is a 5-methylcytosine, and wherein each internucleoside linkage of the test oligonucleotide is a phosphorothioate linkage.

21. The method of claim 20, wherein the test oligonucleotide consists of 20 linked nucleosides.

* * * * *

SEQUENCE LISTING

<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: Antisense Compound

<400> SEQUENCE: 1
accgataacg ttgccggtga cg                                              22

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
acctcctcca tggctcttct                                                 20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
ctaagtcacc ttgttgccat                                                 20

<210> SEQ ID NO 4
<211> LENGTH: 20
<212> TYPE: DNA
<213> ORGANISM: Artificial Sequence
<220> FEATURE:
<223> OTHER INFORMATION: Antisense Compound

<400> SEQUENCE: 4
ttgcttccat cttcctcgtc                                                 20

<210> SEQ ID NO 5
<211> LENGTH: 20
<212> TYPE: DNA
<213> ORGANISM: Artificial Sequence
<220> FEATURE:
<223> OTHER INFORMATION: Antisense Compound

<400> SEQUENCE: 5
ccttccctga aggttcctcc                                                 20

<210> SEQ ID NO 6
<211> LENGTH: 20
<212> TYPE: DNA
<213> ORGANISM: Artificial Sequence
<220> FEATURE:
<223> OTHER INFORMATION: Antisense Compound

<400> SEQUENCE: 6
cgtgtgtctg tgctagtccc                                                 20

<210> SEQ ID NO 7
<211> LENGTH: 20
<212> TYPE: DNA

-continued

```
<213> ORGANISM: Artificial Sequence
<220> FEATURE:
<223> OTHER INFORMATION: Antisense Compound

<400> SEQUENCE: 7
ctgctagcct ctggatttga                                                  20

<210> SEQ ID NO 8
<211> LENGTH: 20
<212> TYPE: DNA
<213> ORGANISM: Artificial Sequence
<220> FEATURE:
<223> OTHER INFORMATION: Antisense Compound

<400> SEQUENCE: 8
cctgctccct ctaatgctgc                                                  20

<210> SEQ ID NO 9
<211> LENGTH: 20
<212> TYPE: DNA
<213> ORGANISM: Artificial Sequence
<220> FEATURE:
<223> OTHER INFORMATION: Antisense Compound

<400> SEQUENCE: 9
cgcaacctcc gccagccgtc                                                  20

<210> SEQ ID NO 10
<211> LENGTH: 20
<212> TYPE: DNA
<213> ORGANISM: Artificial Sequence
<220> FEATURE:
<223> OTHER INFORMATION: Antisense Compound

<400> SEQUENCE: 10
aatgtgcctg ctgtccttga                                                  20

<210> SEQ ID NO 11
<211> LENGTH: 20
<212> TYPE: DNA
<213> ORGANISM: Artificial Sequence
<220> FEATURE:
<223> OTHER INFORMATION: Antisense Compound

<400> SEQUENCE: 11
ctccctctct ccctctctct                                                  20

<210> SEQ ID NO 12
<211> LENGTH: 23
<212> TYPE: DNA
<213> ORGANISM: Artificial Sequence
<220> FEATURE:
<223> OTHER INFORMATION: Antisense Compound

<400> SEQUENCE: 12
aaccgataac gttgccggtg acg                                              23

<210> SEQ ID NO 13
<211> LENGTH: 20
<212> TYPE: DNA
<213> ORGANISM: Artificial Sequence
<220> FEATURE:
<223> OTHER INFORMATION: Antisense Compound

<400> SEQUENCE: 13
gcccagcatc ttggccacag                                                  20
```